US00PP14733P2

(12) United States Plant Patent
Post

(10) Patent No.: US PP14,733 P2
(45) Date of Patent: Apr. 27, 2004

(54) CHRYSANTHEMUM PLANT NAMED 'ZEMBLA YELLOW'

(50) Latin Name: *Chrysanthemum×morifolium*
Varietal Denomination: Zembla Yellow

(75) Inventor: Arie Gerard Post, 's-Gravenzande (NL)

(73) Assignee: Deliflor Royalties B.V., Maasdijk (NL)

( * ) Notice: Subject to any disclaimer, the term of this patent is extended or adjusted under 35 U.S.C. 154(b) by 0 days.

(21) Appl. No.: 10/396,530

(22) Filed: Mar. 25, 2003

(51) Int. Cl.[7] ..... A01H 5/00
(52) U.S. Cl. ..... Plt./289
(58) Field of Search ..... Plt./289

*Primary Examiner*—Bruce R. Campell
*Assistant Examiner*—A. Para
(74) *Attorney, Agent, or Firm*—C. A. Whealy

(57) ABSTRACT

A distinct cultivar of Chrysanthemum plant named 'Zembla Yellow', characterized by its decorative inflorescence form with yellow-colored ray florets; dark green foliage; strong flowering stems; freely flowering habit; short response time; and excellent postproduction longevity.

1 Drawing Sheet

Botanical classification/cultivar designation: *Chrysanthemum×morifolium* cultivar Zembla Yellow.

BACKGROUND OF THE INVENTION

The present invention relates to a new and distinct cultivar of Chrysanthemum plant, botanically known as *Chrysanthemum×morifolium* and referred to by the name 'Zembla Yellow'.

The new Chrysanthemum was discovered by the Inventor in a controlled environment in 's-Gravenzande, The Netherlands, on Nov. 27, 2001, as a naturally-occurring branch mutation of the *Chrysanthemum×morifolium* cultivar Zembla, disclosed in U.S. Plant patent application Ser. No. 10/094,280. The new Chrysanthemum was observed within a population of flowering plants of the cultivar Zembla. The selection of this plant was based on its unique ray floret coloration.

Asexual reproduction of the new Chrysanthemum by terminal cuttings harvested in 's-Gravenzande, The Netherlands since January, 2002, has shown that the unique features of this new Chrysanthemum are stable and reproduced true to type in successive generations.

BRIEF SUMMARY OF THE INVENTION

The cultivar Zembla Yellow has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Zembla Yellow'. These characteristics in combination distinguish 'Zembla Yellow' as a new and distinct cultivar:

1. Decorative inflorescence form with yellow-colored ray florets; typically grown as a spray type.
2. Dark green-colored foliage.
3. Strong flowering stems.
4. Freely flowering habit.
5. Short response time.
6. Excellent postproduction longevity.

Plants of the new Chrysanthemum are most similar to plants of the parent cultivar Zembla; however in side-by-side comparisons conducted in 's-Gravenzande, The Netherlands, plants of the new Chrysanthemum differed from plants of the cultivar Zembla in the following characteristics:

1. Leaf venation color of plants of the new Chrysanthemum was duller green than leaf venation color of plants of the cultivar Zembla.
2. Ray florets of plants of the new Chrysanthemum were yellow in color whereas ray florets of plants of the cultivar Zembla were white in color.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the actual colors of the new Chrysanthemum.

The photograph at the top of the sheet comprises a side perspective view of a typical flowering stem of 'Zembla Yellow'.

The photograph at the bottom of the sheet comprises a close-up view of the upper and lower surfaces of typical leaves of 'Zembla Yellow'.

DETAILED BOTANICAL DESCRIPTION

In the following description, color references are made to The Royal Horticultural Society Colour Chart, 1995 Edition, except where general terms of ordinary dictionary significance are used. The aforementioned photographs, following observations and measurements describe plants grown in ground beds in 's-Gravenzande, The Netherlands, under commercial practice in a glass-covered greenhouse. Plants were initially given short nyctoperiods followed by long nyctoperiods to induce flower initiation and development. Average day and night temperatures were 18 and 19° C., respectively. Plants were grown as single-stem spray types and were about 11 weeks old when the photographs and description were taken.

Botanical classification: *Chrysanthemum×morifolium* cultivar Zembla Yellow.

Commercial classification: Cut Chrysanthemum with decorative inflorescence form; typically grown as a spray-type.

Parentage: Naturally-occurring branch mutation of *Chrysanthemum×morifolium* cultivar Zembla, disclosed in U.S. Plant patent application Ser. No. 10/094,280.

Propagation:

*Type.*—Terminal tip cuttings.

*Time to initiate roots, summer.*—About 5 days at 20° C.

*Time to initiate roots, winter.*—About 6 days at 20° C.

*Root description.*—Fine, fibrous and well-branched.

Plant description:

*Appearance.*—Herbaceous cut Chrysanthemum with decorative inflorescence form; typically grown as a spray type. Upright with strong stems.

*Growth rate.*—Moderate; vigorous.

*Crop time.*—For cut flowers, about 11 weeks are required to produce flowering stems.

*Flowering stem description.*—Length: About 80 cm. Diameter, at base: About 6 mm. Strength: Strong. Aspect: Upright. Branching habit: Plants are typically grown as single stems. Color: 146C.

*Foliage description.*—Arrangement: Alternate. Length: About 12 to 15 cm. Width: About 6.5 to 7 cm. Apex: Mucronate. Base: Obtuse to truncate. Margin: Palmately lobed. Texture, upper and lower surfaces: Rough; pubescent. Petiole length: About 1.7 to 2.5 cm. Color: Developing foliage, upper surface: Between 139A and 147A. Developing foliage, lower surface: 137C. Fully expanded foliage, upper surface: 147A. Fully expanded foliage, lower surface: 147B. Venation, upper and lower surfaces: 143C. Petiole: 144A.

Inflorescence description:

*Appearance.*—Decorative inflorescence form. Inflorescences borne on terminals, arising from leaf axils. Ray and disc florets arranged acropetally on the receptacle.

*Flowering response.*—Under natural conditions, plant typically flower in November in the Northern Hemisphere. At other times of the year, inflorescence initiation and development can be induced under long nyctoperiod conditions (at least 13.5 hours of darkness). Early flowering; plants exposed to short nyctoperiods conditions after planting followed by photoinductive long nyctoperiod conditions flower about 7.5 to 8 weeks later.

*Postproduction longevity.*—Inflorescences will maintain good substance and form for about five weeks on the plant and for about three weeks after harvesting cut flowering stems.

*Quantity of inflorescences per flowering stem.*—About 10 to 14.

*Inflorescence size.*—Diameter: About 9 cm. Depth (height): About 2.5 cm. Diameter of disc: Less than 5 mm; inconspicuous.

*Inflorescence buds.*—Length: About 8 mm. Diameter: About 1.1 cm. Shape: Oblate. Color: 138A.

*Ray florets.*—Length: About 4.5 cm. Width: About 1.7 cm. Shape: Elongated oblong. Apex: Rounded to slightly emarginate. Base: Acute to attenuate. Margin: Entire. Texture: Smooth, glabrous. Number of ray florets per inflorescence: About 260. Color: When opening and fully opened, upper surface: 5C. When opening and fully opened, lower surface: 5D.

*Disc florets.*—Shape: Oblong, tubular. Length: About 4 mm. Width: About 1 mm. Number of disc floret per inflorescence: About 10. Color, immature and mature: 20A; apex, 145C.

*Peduncles.*—Length, terminal peduncle: About 10.5 cm. Length, fourth peduncle: About 9.5 cm. Diameter: About 2 to 3 mm. Angle: About 50° to main stem. Texture: Pubescent. Color: 146B.

*Reproductive organs.*—Androecium: Present on disc florets only. Anther color: 12A. Amount of pollen: Moderate. Pollen: 12A. Gynoecium: Present on both ray and disc florets.

*Seed.*—Seed production has not been observed.

Disease/pest resistance: Resistance to known Chrysanthemum pathogens and pests has not been observed on plants of the new Chrysanthemum.

It is claimed:

1. A new and distinct cultivar of Chrysanthemum plant named 'Zembla Yellow', as illustrated and described.

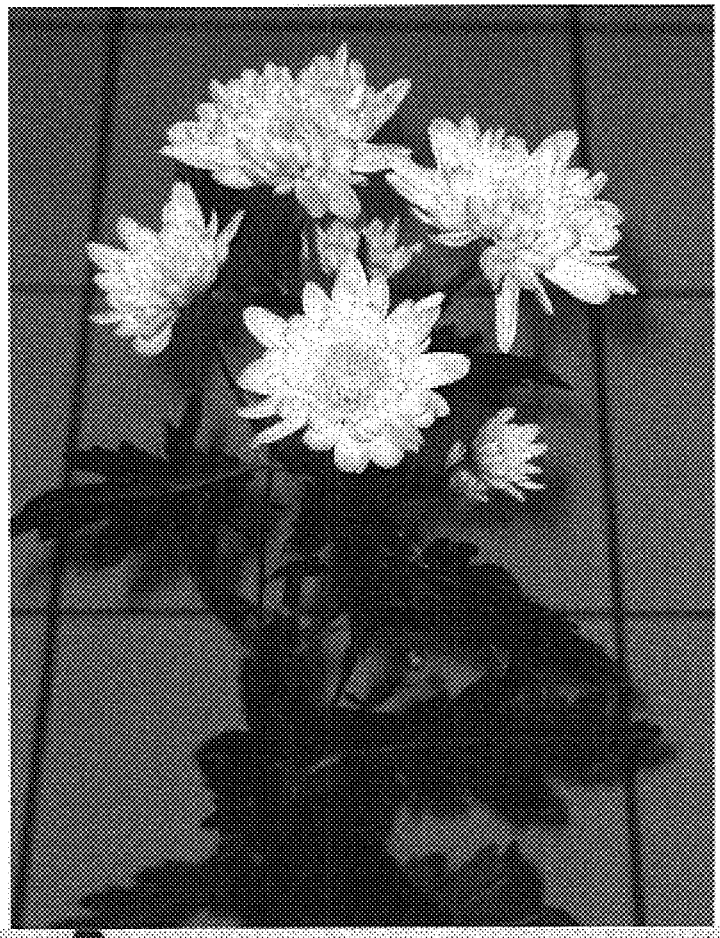
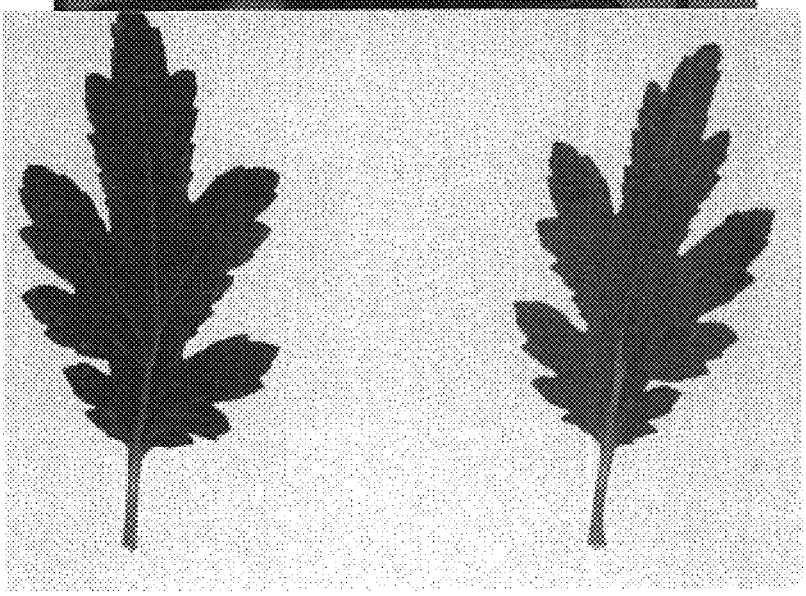

* * * * *